United States Patent [19]

Quentin-Millet et al.

[11] Patent Number: 5,618,540
[45] Date of Patent: Apr. 8, 1997

[54] SUBUNIT VACCINE AGAINST *NEISSERIA MENINGITIDIS* INFECTIONS AND CORRESPONDING SUBUNITS IN THE PURIFIED STATE

[75] Inventors: Marie J. Quentin-Millet, Villeurbanne; Ling Lissolo, Marcy L'Etoile, both of France

[73] Assignee: Pasteur Merieux Serums et Vaccins, Lyons, France

[21] Appl. No.: 64,174

[22] PCT Filed: Sep. 29, 1992

[86] PCT No.: PCT/FR92/00904

§ 371 Date: May 25, 1993

§ 102(e) Date: May 25, 1993

[87] PCT Pub. No.: WO93/07172

PCT Pub. Date: Apr. 15, 1993

[30] Foreign Application Priority Data

Oct. 3, 1991 [FR] France ................................. 91 12176

[51] Int. Cl.⁶ ........................................ A61K 39/095
[52] U.S. Cl. ........................ 424/250.1; 424/249.1; 435/871
[58] Field of Search ....................... 424/92, 250.1, 424/249.1; 435/871; 530/400

[56] References Cited

FOREIGN PATENT DOCUMENTS

| 90/12591 | 11/1990 | WIPO |
| 9203467 | 3/1992 | WIPO |

OTHER PUBLICATIONS

Griffiths et al, FEMS Microbiology Letters 69:31–36, 1990.
Zollinger et al, Infect & Immunity 40(1): 257–264, 1983.
Zollinger et al, Transactions of the Royal Society of Tropical Medicine & Hygiene 85: Supplement 1, 37–43, 1991.
Pettersson et al, Infection & Immunity 58(9):3036–3041, 1990.
Geysen et al, J. Molecular Recognition, 1(1): 32–41, 1988.
Saukkonen et al, Vaccine 7: 325–328, 1989.
Schuyvers et al, Molecular Microbiology 2(2): 281–288, 1988.
Nirupama Banerjee-Bhatnagar et al., "Expression of *Neisseria meningitidis* Iron–Regulated Outer Membrane Proteins, Including a 70–Kilodalton Transferrin Receptor, and Their Potential for Use as Vaccines," *Infection and Immunity*, vol. 58, No. 9, 1990, pp. 2875–2881.
Anthony B. Schryvers et al, "Identification and Characterization of the Human Lactoferrin–Binding Protein from *Neisseria meningitidis*," *Infection and Immunity*, vol. 56, No. 5, 1988, pp. 1144–1149.
Anthony B. Schryvers et al, Chemical Abstract No. 150244, "Identification and Characterization of the Transferrin Receptor from *Neisseria meningitidis*," by Schryvers et al., *Microbial Biochem.*, vol. 111, No. 17, 1989, p. 389.

Primary Examiner—James C. Housel
Assistant Examiner—Julie Krsek-Staples
Attorney, Agent, or Firm—Burns, Doane, Swecker & Mathis, L.L.P.

[57] ABSTRACT

The present invention relates to the lower molecular weight subunit of the human transferrin receptor of a strain of *N. meningitidis*, in purified form, as well as to a vaccinal pharmaceutical composition intended for the prevention or attenuation of the effects of an *N. meningitidis* infection, containing the said subunit in purified form.

15 Claims, No Drawings

SUBUNIT VACCINE AGAINST *NEISSERIA MENINGITIDIS* INFECTIONS AND CORRESPONDING SUBUNITS IN THE PURIFIED STATE

The present invention relates to a vaccinal pharmaceutical composition intended for the prevention of meningitis caused by *Neisseria meningitidis*.

Generally speaking, meningitis is either of viral origin or of bacterial origin. The bacteria mainly responsible are *N. meningitidis* and *Haemophilus influenzae*, which are implicated, respectively, in approximately 40 and 50% of cases of bacterial meningitis.

*N. meningitidis* accounts for approximately 600 to 800 cases of meningitis per annum in France. In the USA, the number of cases amounts to approximately 2,500 to 3,000 per annum.

The species *N. meningitidis* is subdivided into serogroups according to the nature of the capsular polysaccharides. Although a dozen serogroups exist, 90% of cases of meningitis are attributable to 3 serogroups: A, B and C.

There are effective vaccines based on capsular polysaccharides to prevent meningitis caused by *N. meningitidis* serogroups A and C. These polysaccharides, as such, exhibit little or no immunogenicity in infants under 2 years of age, and do not induce immune memory. However, these drawbacks may be overcome by conjugating these polysaccharides to a carrier protein.

On the other hand, the polysaccharide of *N. meningitidis* group B exhibits little or no immunogenicity in man, either in conjugated or in unconjugated form. Thus, it is seen to be highly desirable to seek a vaccine against meningitis induced by *N. meningitidis*, in particular of serogroup B, other than a vaccine based on polysaccharide.

To this end, various proteins of the outer membrane of *N. meningitidis* have already been proposed. Special attention has focused on the membrane receptor for human transferrin.

Generally speaking, the large majority of bacteria require iron for their growth, and have developed specific systems for acquiring this metal. As regards *N. meningitidis* in particular, which is a strict pathogen of man, the iron can be abstracted only from human iron-transport proteins such as transferrin and lactoferrin, since the amount of iron in free form is negligible in man (of the order of $10^{-18}$ M), and in any case insufficient to permit bacterial growth.

Thus, *N. meningitidis* possesses a human transferrin receptor and a human lactoferrin receptor, which enable it to bind these iron-chelating proteins and thereafter to take up the iron needed for its growth.

The transferrin receptor of *N. meningitidis* strain B16B6 has been purified by Schryvers et al. (WO 90/12591) from a membrane extract. This protein as purified evidently consists essentially of two types of polypeptide: a polypeptide of high apparent molecular weight of 100 kD and a polypeptide of lower apparent molecular weight of approximately 70 kD, as visualised after polyacrylamide gel electrophoresis in the presence of SDS.

The product of the purification carried out, in particular, by Schryvers is referred to, by arbitrary definition and for the requirements of the present patent application, as the transferrin receptor, and the polypeptides of which it consists are referred to as subunits. In the text below, the subunits of high molecular weight and of lower molecular weight are referred to as Tbp1 and Tbp2, respectively.

Surprisingly, it has now been found that the high molecular weight subunit could not induce the production of neutralising type antibodies. Only the smaller of the 2 subunits of the receptor appears to be capable of fulfilling this function.

Consequently, the invention provides for:

i) The lower molecular weight subunit of the human transferrin receptor of a strain of *N. meningitidis*, a fragment or an analogue of the said subunit, in purified form; that is to say dissociated and isolated from the high molecular weight subunit of the said receptor; and ii) A vaccinal pharmaceutical composition which comprises, as therapeutic agent, the lower molecular weight subunit of the human transferrin receptor of at least one strain of *N. meningitidis*, a fragment or an analogue of the said subunit; in the absence of the high molecular weight subunit of the said receptor;

iii) The therapeutic use of the lower molecular weight subunit of the human transferrin receptor of at least one strain of *N. meningitidis*, a fragment or an analogue of the said subunit; in the absence of the high molecular weight subunit of the said receptor; and iv) A method of vaccination against *N. meningitidis* infections, which comprises the act of administering an effective amount, from a therapeutic standpoint, of the lower molecular weight subunit of the human transferrin receptor of at least one strain of *N. meningitidis*, a fragment or an analogue of the said subunit, in the absence of the high molecular weight subunit of the said receptor, to a subject requiring such a treatment.

Generally speaking, the lower molecular weight subunit may be obtained in purified form (that is to say dissociated and isolated from the high molecular weight subunit), in particular, from a transferrin receptor. The latter may be isolated from a strain of *N. meningitidis* previously cultured in a medium deficient in iron in free form, in particular according to the method of Schryvers et al., WO 90/12591, described in a similar manner in Schryvers et al., Infect. Immun. (1988) 56 (5):1144. The purified receptor is then subjected to the action of a strongly denaturing agent such as 8M urea or 6M guanidine HCl. The dissociated subunits are finally separated by standard chromatographic methods such as ion exchange chromatography, hydrophobic chromatography or gel filtration.

Alternatively, the lower molecular weight subunit may be produced by employing genetic engineering techniques. The DNA fragment coding for this subunit may be expressed in a heterologous expression system (e.g. bacterium, yeast, mammalian cell). The subunit is, in this case, collected from a culture and purified. These methods are, in addition, entirely suited to the production of fragments or analogues of the subunit.

"Fragment of the lower molecular weight subunit" is understood to mean a peptide having an amino acid sequence which is included in the sequence of the subunit. "Analogue of the lower molecular weight subunit" is understood to mean a protein having an amino acid sequence which exhibits an at least 80%, preferably at least 90% and, as an absolute preference, at least 95% homology with the sequence of the subunit. For the purposes of the present invention, it should be clearly understood that such a fragment or such an analogue must retain the immunogenic properties of the subunit.

With respect to the subunit Tbp2, *N. meningitidis* strains may be divided into 2 major groups:

those in which the subunit Tbp2 has a molecular weight of 65 to 74 kD approximately (strains termed type 2394); and those in which the subunit Tbp2 has a molecular weight of 75 to 90 kD approximately (strains termed type 2169).

Generally speaking, the lower molecular weight subunit which is useful for the purposes of the present invention can originate from a strain of *N. meningitidis* of any serogroup. Advantageously, it originates from a strain of *N. meningitidis* serogroup B. According to an absolutely preferred aspect of the invention, it originates from *N. meningitidis* strain B16B6 also referred to as 2394 (B:2a:P1.2:L2.3), or M982 also referred to as 2169 (B:9:P1.9:L3.7), which are available to the public from the Collection of the Pasteur Institute, 25 rue du Dr Roux 75015 Paris under the respective registration numbers CIP 7908 and CIP 7917.

As an example, the subunit Tbp2 of the strains 2394 and 2169 is described by reference to its amino acid sequence as shown in the sequence identifiers Nos. 1 and (SEQ ID Nos. 1 and 2). The apparent molecular weights of these subunits are, respectively, 68–70 and 87 kD approximately, as visualised after polyacrylamide gel electrophoresis in the presence of SDS.

A pharmaceutical composition according to the invention is, in particular, useful for preventing or attenuating the effects of an *N. meningitidis* infection.

A pharmaceutical composition according to the invention may be manufactured in a conventional manner. In particular, the therapeutic agent according to the invention is combined with a diluent or vehicle which is acceptable from a pharmaceutical standpoint. A composition according to the invention may be administered by any conventional route in use in the vaccine field, especially subcutaneously, intramuscularly or intravenously, for example in the form of an injectable suspension. The administration can take place in a single dose or in a dose repeated one or several times after a certain time interval. The appropriate dosage varies in accordance with various parameters, for example with the individual being treated or with the mode of administration.

Lastly, a composition according to the invention can contain one or more lower molecular weight subunits depending on whether the latter originate from different strains of *N. meningitidis*. Thus, according to a particular aspect of the invention, an advantageous pharmaceutical composition comprises the lower molecular weight subunit of the human transferrin receptor of a type 2394 strain (molecular weight of 65 to 74 kD) and the lower molecular weight subunit of the human transferrin receptor of a type 2169 strain (molecular weight of 75 to 90 kD).

Preferably, a composition according to the invention comprises the lower molecular weight subunit of the human transferrin receptor of the strain 2394 (molecular weight: 68–70 kD) and the lower molecular weight subunit of the human transferrin receptor of the strain 2169 (molecular weight: 87 kD).

The invention is described in detail in the examples below.

EXAMPLE 1: Purification of the lower molecular weight subunit of the transferrin receptor from the strain 2394, by ion exchange chromatography 1A - Culture A lyophilisate of *N. meningitidis* strain 2394 is taken up in approximately 1 ml of Mueller-Hinton broth (MHB, Difco). The bacterial suspension is then plated out on Mueller-Hinton solid medium containing cooked blood (5%).

After 24 h of incubation at 37° C. in an atmosphere containing 10% of $CO_2$, the bacterial lawn is collected in order to inoculate 150 ml of MHB pH 7.2, distributed in 3 250-ml Erlenmeyers. Incubation is carried out for 3 h at 37° C. with stirring. Each of the 3 cultures so produced permits the inoculation of 400 ml of MHB pH 7.2 supplemented with 30 μM of ethylenediaminedi-(o-hydroxyphenylacetic acid) (EDDA, Sigma), which is a chelating agent for iron in free form.

After 16 h of culture at 37° C. with stirring, the cultures are monitored for their purity by microscopic observation after Gram staining. The suspension is centrifuged and the pellet containing the microbes is weighed and stored at −20° C.

1B—Purification

The purification method is essentially that described by Schryvers et al. (supra).

The bacterial pellet obtained in 1A is thawed and then resuspended in 200 ml of 50 mM Tris-HCl buffer, pH 8.0 (buffer A). The suspension is centrifuged for 20 min at 15,000×g at 4° C. The pellet is recovered and then resuspended in buffer A at a final concentration of 150 g/l. 150-ml fractions are treated for 8 min at 800 bars in a cell lyser working under high pressure (Rannie, model 8.30H). The cell lysate thereby obtained is centrifuged for 15 min at 4° C. at 15,000×g. The supernatant is recovered and then centrifuged for 75 min at 4° C. at 200,000×g.

After removal of the supernatant, the pellet is taken up in buffer A and, after protein assay by the Lowry method, the concentration of the suspension is adjusted to 5 mg/ml.

1.75 mg of biotinylated human transferrin are then added to 1.4 ml of the membrane suspension according to the method described in Schryvers. The final concentration of the membrane fraction is 4 mg/ml. The mixture is incubated for 1 hour at 37° C. and then centrifuged at 100,000×g for 75 minutes at 4° C. The membrane pellet is taken up with buffer A containing 0.1M NaCl, and incubated for 60 min at room temperature.

After solubilisation, a certain volume of 30% (w/v) Sarkosyl (N-lauroylsarcosine, Sigma) and of 500 mM EDTA are added to this suspension so that the final concentrations of Sarkosyl and EDTA are 0.5% and 5 mM, respectively. After incubation for 15 min at 37° C. with stirring, 1 ml of streptavidin-agarose resin (Pierce), previously washed in buffer A, is added. The suspension is incubated for 15 min at room temperature and then centrifuged at 1,000×g for 10 min. The resin is then packed in a column and the direct eluate is discarded.

The resin is washed with 3 column volumes of 50 mM Tris-HCl buffer pH 8.0 containing 1M NaCl, 10 mM EDTA, 0.5% Sarkosyl (buffer B), and then with one column volume of buffer B containing 750 mM guanidine HCl. The transferrin receptor is then eluted with 50 mM Tris-HCl buffer pH 8.0 containing 1M NaCl, 10 mM EDTA, 0.05% Sarkosyl and 2M guanidine HCl. The eluate is collected in fractions whose volume corresponds to 1 Vol. in tubes containing 1 Vol. of 50 mM Tris-HCl pH 8.0, 1M NaCl. The optical density of the eluate at 280 nm is measured at the column outlet using a UV detector.

The fractions corresponding to the elution peak are collected, dialysed against 10 mM phosphate buffer, pH 8.0 containing 0.5M urea and then concentrated using an Amicon type concentration cell equipped with a membrane whose cut-off threshold is 10,000 daltons to a final concentration of approximately 3 mg of protein/ml.

A certain amount of urea is added to the concentrated solution so that the final urea concentration is 8M, the final concentration of the protein solution remaining between 2 and 3 mg/ml. The solution is incubated for 6 days at 4° C.

The mixture is then chromatographed on an anion exchange resin (Q Sepharose, Pharmacia) previously equilibrated in 50 mM Tris-HCl buffer pH 8.0 containing 5M urea.

Under these conditions, the high molecular weight subunit (Tbp1) is collected directly in the direct eluate, while the lower molecular weight subunit (Tbp2) is eluted with a linear gradient of 0–1M NaCl in buffer A containing 0.5% Sarkosyl and 5M urea. The optical density at 280 nm is measured at the column outlet using a UV detector.

The fractions corresponding to the elution peak are collected, dialysed against 10 mM phosphate buffer, pH 8.0 containing 0.05% Sarkosyl and lyophilised. The lyophilisate is taken up in water at a 10-fold higher concentration. The solution is dialysed a second time against 50 mM phosphate buffer pH 8.0 containing 0.05% Sarkosyl (buffer C), and the solution is then filtered through a membrane of porosity 0.22 μm.

The protein content is determined and adjusted to 1 mg/ml by adding buffer C, under aseptic conditions. This preparation is stored at −70° C.

EXAMPLE 2: Purification of the lower molecular weight subunit of the transferrin receptor from the strain 2169

Culturing of the strain 2169 and purification of the lower molecular weight subunit of the transferrin receptor are performed under conditions identical to those described in Example 1.

EXAMPLE 3: Purification of the lower molecular weight subunit of the transferrin receptor from *N. meningitidis* strain 2394 by hydrophobic chromatography Culturing of *N. meningitidis* strain 2394, as well as the purification steps up to the point of preparation of the membrane suspension, are performed under conditions identical to those described in Example 1.

To one volume of the membrane suspension, an identical volume of 50 mM Tris-HCl pH 8.0 containing 2M NaCl, 20 mM EDTA, 1% (w/v) Sarkosyl is added. The mixture is incubated for 15 min at 37° C. with gentle agitation. One volume of this suspension is then brought into contact with an identical volume of Sepharose 4B resin coupled to human transferrin. This affinity resin was coupled by grafting human transferrin (Sigma, St Louis USA) to Sepharose 4B-CNBr (Pharmacia) according to manufacturer's recommendations. The density of the ligand is 5 mg transferrin/ml of resin. Contact takes place in a bath for 1 h at room temperature with gentle rotary stirring. The resin is then packed in a column and the direct eluate is discarded.

The resin is washed with 3 column volumes of 50 mM Tris-HCl buffer pH 8.0 containing 1M NaCl, 10 mM EDTA, 0.5% Sarkosyl (buffer B), and then with one column volume of buffer B containing 750 mM guanidine HCl. The transferrin receptor is then eluted with 50 mM Tris-HCl buffer pH 8.0, 1M NaCl, 10 mM EDTA, 0.05% Sarkosyl and 2M guanidine HCl. The optical density of the eluate at 280 nm is measured at the column outlet using an UV detector. The fractions corresponding to the elution peak are pooled and the protein is precipitated by adding three volumes of cooled ethanol.

After overnight incubation at +4° C., the protein is collected by centrifugation for one hour at 10,000×g. The precipitate is taken up with a certain volume of 10 mM phosphate buffer pH 7.0 containing 0.5M NaCl, 5M guanidine HCl (buffer D) so that the final protein concentration is approximately 1 mg/ml. The solution is brought into contact with phenyl-Sepharose resin (Pharmacia) previously equilibrated with the same buffer. Incubation takes place in a bath with rotary stirring for 2 hours at room temperature. The gel is then packed in a column.

Under these conditions, the high molecular weight subunit (Tbp1) is collected in the direct eluate, while the lower molecular weight subunit (Tbp2) is bound to the resin. The column is rinsed with three volumes of buffer D and then with 5 volumes of 10 mM phosphate buffer pH 7.0. Tbp2 is eluted with 10 mM phosphate buffer pH 7.0 containing 0.5% of Sarkosyl. The excess Sarkosyl contained in the Tbp2 elution buffer is removed by ethanol precipitation, and the protein is then taken up in 50 mM phosphate buffer pH 8.0 containing 0.05% Sarkosyl (buffer C).

The solution is then filtered through a membrane of porosity 0.22 µm. The protein content is determined and adjusted to 1 mg/ml by adding buffer C, under aseptic conditions. This preparation is stored at −70° C.

EXAMPLE 4: Purification of the lower molecular weight subunit from *N. meningitidis* strain 2169 by hydrophobic chromatography Culturing of *N. meningitidis* strain 2169 and purification of the lower molecular weight subunit of the transferrin receptor (Tbp2) are performed under conditions identical to those described in Example 3.

EXAMPLE 5: Demonstration of the importance of the lower molecular weight subunit as a vaccinal agent The bactericidal activity of sera specifically directed towards the lower molecular weight subunit (Tbp2) of the transferrin receptor of *N. meningitidis* strains 2394 and 2169 is evaluated.

For this purpose, the Tbp2 subunits were prepared by hydrophobic chromatography as described in Examples 3 and 4.

Albino New Zealand rabbits receive subcutaneously and intramuscularly 50 µg of Tbp2 isolated from the strain 2394 or 2169, in the presence of Freund's complete adjuvant (Difco). 21 and 42 days after the first injection, the rabbits again receive 50 µg of purified subunit Tbp2, but this time in the presence of Freund's incomplete adjuvant. 15 days after the last injection, the animals' serum is withdrawn, then decomplemented and filtered through a membrane of porosity of 0.45 µm.

A dilution series of each of the antisera, anti-Tbp2 2394 and anti-Tbp2 2169, is prepared in M199 medium (Gibco). 200 µl of each dilution are placed in the wells of a microtitration plate (8×12 in.). A control test is carried out with 200 µl of M199 medium. Into each of the wells there are added (i) 100 µl of a culture in the exponential growth phase of a strain of *N. meningitidis*, in Mueller-Hinton medium containing 30 µM EDDA and (ii) 100 µl of complement (young rabbit serum, diluted).

After 30 min of incubation at 37° C. with gentle stirring, 1 ml of Mueller-Hinton medium containing 1 ml of Noble agar in the supercooled state is added into each well. After solidification of the medium, incubation is carried out for 18–24 hours at 37° C.; the number of colony forming units in each well is then evaluated. The reciprocal of the final dilution of antiserum in the presence of which a 50% lysis is observed relative to the control corresponds to the bactericidal titre.

The results are presented in the table below:

| Bactericidal activity of the anti-Tbp2 2394 and anti-Tbp2 2169 antisera ||||| 
| *Neisseria meningitidis* || Batericidal activity ||||
| | | Anti-Tbp2 2394 serum || Anti-Tbp2 2169 serum ||
| Strain | serogroup/ type/subtype | preimmunisation | postimmunisation | preimmunisation | postimmunisation |
|---|---|---|---|---|---|
| 2394 | B, 2a, P1.2 | <8 | 512 | — | — |
| 2169 | B, 9, P1.9 | — | — | <8 | 128 |

The antiserum is bactericidal with respect to the strain from which Tbp2 has been purified, demonstrating that the anti-Tbp2 antibodies induced are functional and have the capacity to lyse the bacterium in the presence of complement.

EXAMPLE 6: Vaccinal pharmaceutical composition intended for preventing *N. meningitidis* infections The sterile solution obtained in Example 3 or 4 is thawed. In order to prepare one liter of vaccine containing 200 μg/ml of an active principle, the following solutions are mixed under sterile conditions:

| | |
|---|---|
| Solution containing the subunit Tbp2 of the 2394 (or 2169) receptor at a concentration of 1 mg/ml in buffer C | 200 ml |
| Buffered physiological saline (PBS), pH 6.0 | 300 ml |
| Aluminium hydroxide containing 10 mg Al$^{+++}$/ml | 50 ml |
| Merthiolate, 1% (w/v) in PBS | 10 ml |
| PBS qs | 1,000 ml |

EXAMPLE 7: Vaccinal pharmaceutical composition intended for preventing *N. meningitidis* infections The sterile solutions obtained in Examples 3 and 4 are thawed. In order to prepare one liter of vaccine containing 100 μg/ml of each of the active principles, the following solutions are mixed under sterile conditions:

| | |
|---|---|
| Solution containing the subunit Tbp2 of the 2394 receptor at a concentration of 1 mg/ml in buffer C | 100 ml |
| Solution containing the subunit Tbp2 of the 2169 receptor at a concentration of 1 mg/ml in buffer C | 100 ml |
| Buffered physiological saline (PBS), pH 6.0 | 300 ml |
| Aluminium hydroxide containing 10 mg Al$^{+++}$/ml | 50 ml |
| Merthiolate, 1% (w/v) in PBS | 10 ml |
| PBS qs | 1,000 ml |

We claim:

1. The lower molecular weight subunit of the human transferrin receptor of a strain of *N. meningitidis*, in substantially purified form and in the absence of the higher molecular weight subunit of said receptor.

2. The lower molecular weight subunit of the human transferrin receptor of a strain of *N. meningitidis* serogroup B, in substantially purified form and in the absence of the higher molecular weight subunit of said receptor.

3. The lower molecular weight subunit of the human transferrin receptor of a strain of *N. meningitidis*, in substantially purified form and in the absence of the higher molecular weight subunit of receptor; the said subunit having a molecular weight of 65 to 74 kD approximately.

4. The lower molecular weight subunit of the human transferrin receptor of a strain of *N. meningitidis* strain 2394, in substantially purified form and in the absence of the higher molecular weight subunit of said receptor.

5. The lower molecular weight subunit of the human transferrin receptor of a strain of *N. meningitidis*, in substantially purified form and in the absence of the higher molecular weight subunit of said receptor; the said subunit having a molecular weight of 75 to 90 kD approximately.

6. The lower molecular weight subunit of the human transferrin receptor of an *N. meningitidis* strain 2169, in substantially purified form and in the absence of the higher molecular weight subunit of said receptor.

7. A vaccinal pharmaceutical composition which comprises, as therapeutic agent, the lower molecular weight subunit of the human transferrin receptor of at least one strain of N. meningitidis; in the absence of the high molecular weight subunit of the said receptor.

8. A pharmaceutical composition according to claim 7, which comprises the lower molecular weight subunit of the human transferrin receptor of at least one strain of N. meningitidis serogroup B.

9. A pharmaceutical composition according to claim 7, which comprises, as therapeutic agent, the lower molecular weight subunit of the human transferring receptor of a strain of N. meningitidis; the said subunit having a molecular weight of 65 to 74 kD approximately.

10. A pharmaceutical composition according to claim 9, which comprises, as therapeutic agent, the lower molecular weight subunit of the human transferrin receptor of N. meningitidis 2394.

11. A pharmaceutical composition according to claim 7, which comprises, as therapeutic agent, the lower molecular weight subunit of the human transferrin receptor of a strain of N. meningitidis; the said subunit having a molecular weight of 75 to 90 kD approximately.

12. A pharmaceutical composition according to claim 11, which comprises, as therapeutic agent, the lower molecular weight subunit of the human transferrin receptor of N. meningitidis 2169.

13. A pharmaceutical composition according to claim 7, which comprises, as therapeutic agent:

i) a first lower molecular weight subunit of the human transferrin receptor of a first strain of N. meningitidis; the said first subunit having a molecular weight of 65 to 74 kD approximately; and ii) a second lower molecular weight subunit of the human transferrin receptor of a second strain of N. meningitidis; the said second subunit having a molecular weight of 75 to 90 kD approximately;

in the absence of the high molecular weight subunit of the said receptor of the said first and second strains of N. meningitidis.

14. A pharmaceutical composition according to claim 13, which comprises, as therapeutic agent:

i) the lower molecular weight subunit of the human transferrin receptor of N. meningitidis 2394; and ii) the lower molecular weight subunit of the human transferrin receptor of N. meningitidis 2169;

in the absence of the high molecular weight subunit of the said receptor of N. meningitidis strains 2394 and 2169.

15. A vaccinal pharmaceutical composition which comprises, as a therapeutic agent, the lower molecular weight subunit of the human transferrin receptor of a strain of N. meningitidis, in the absence of the high molecular weight subunit of said receptor.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 579 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Cys Leu Gly Gly Gly Gly Ser Phe Asp Leu Asp Ser Val Glu Thr Val
 1               5                  10                  15

Gln Asp Met His Ser Lys Pro Lys Tyr Glu Asp Glu Lys Ser Gln Pro
            20                  25                  30

Glu Ser Gln Gln Asp Val Ser Glu Asn Ser Gly Ala Ala Tyr Gly Phe
        35                  40                  45

Ala Val Lys Leu Pro Arg Arg Asn Ala His Phe Asn Pro Lys Tyr Lys
    50                  55                  60

Glu Lys His Lys Pro Leu Gly Ser Met Asp Trp Lys Lys Leu Gln Arg
65                  70                  75                  80

Gly Glu Pro Asn Ser Phe Ser Glu Arg Asp Glu Leu Glu Lys Lys Arg
                85                  90                  95

Gly Ser Ser Glu Leu Ile Glu Ser Lys Trp Glu Asp Gly Gln Ser Arg
            100                 105                 110

Val Val Gly Tyr Thr Asn Phe Thr Tyr Val Arg Ser Gly Tyr Val Tyr
        115                 120                 125

Leu Asn Lys Asn Asn Ile Asp Ile Lys Asn Asn Ile Val Leu Phe Gly
    130                 135                 140

Pro Asp Gly Tyr Leu Tyr Tyr Lys Gly Lys Glu Pro Ser Lys Glu Leu
145                 150                 155                 160

Pro Ser Glu Lys Ile Thr Tyr Lys Gly Thr Trp Asp Tyr Val Thr Asp
                165                 170                 175
```

```
Ala Met Glu Lys Gln Arg Phe Glu Gly Leu Gly Ser Ala Ala Gly Gly
            180                 185                 190
Asp Lys Ser Gly Ala Leu Ser Ala Leu Glu Glu Gly Val Leu Arg Asn
            195                 200                 205
Gln Ala Glu Ala Ser Ser Gly His Thr Asp Phe Gly Met Thr Ser Glu
            210                 215                 220
Phe Glu Val Asp Phe Ser Asp Lys Thr Ile Lys Gly Thr Leu Tyr Arg
225                 230                 235                 240
Asn Asn Arg Ile Thr Gln Asn Asn Ser Glu Asn Lys Gln Ile Lys Thr
                245                 250                 255
Thr Arg Tyr Thr Ile Gln Ala Thr Leu His Gly Asn Arg Phe Lys Gly
            260                 265                 270
Lys Ala Leu Ala Ala Asp Lys Gly Ala Thr Asn Gly Ser His Pro Phe
            275                 280                 285
Ile Ser Asp Ser Asp Ser Leu Glu Gly Gly Phe Tyr Gly Pro Lys Gly
            290                 295                 300
Glu Glu Leu Ala Gly Lys Phe Leu Ser Asn Asp Asn Lys Val Ala Ala
305                 310                 315                 320
Val Phe Gly Ala Lys Gln Lys Asp Lys Lys Asp Gly Glu Asn Ala Ala
            325                 330                 335
Gly Pro Ala Thr Glu Thr Val Ile Asp Ala Tyr Arg Ile Thr Gly Glu
            340                 345                 350
Glu Phe Lys Lys Glu Gln Ile Asp Ser Phe Gly Asp Val Lys Lys Leu
            355                 360                 365
Leu Val Asp Gly Val Glu Leu Ser Leu Leu Pro Ser Glu Gly Asn Lys
            370                 375                 380
Ala Ala Phe Gln His Glu Ile Glu Gln Asn Gly Val Lys Ala Thr Val
385                 390                 395                 400
 Cys Cys Ser Asn Leu Asp Tyr Met Ser Phe Gly Lys Leu Ser Lys Glu
            405                 410                 415
Asn Lys Asp Asp Met Phe Leu Gln Gly Val Arg Thr Pro Val Ser Asp
            420                 425                 430
Val Ala Ala Arg Thr Glu Ala Lys Tyr Arg Gly Thr Gly Thr Trp Tyr
            435                 440                 445
Gly Tyr Ile Ala Asn Gly Thr Ser Trp Ser Gly Glu Ala Ser Asn Gln
            450                 455                 460
Glu Gly Gly Asn Arg Ala Glu Phe Asp Val Asp Phe Ser Thr Lys Lys
465                 470                 475                 480
Ile Ser Gly Thr Leu Thr Ala Lys Asp Arg Thr Ser Pro Ala Phe Thr
            485                 490                 495
Ile Thr Ala Met Ile Lys Asp Asn Gly Phe Ser Gly Val Ala Lys Thr
            500                 505                 510
Gly Glu Asn Gly Phe Ala Leu Asp Pro Gln Asn Thr Gly Asn Ser His
            515                 520                 525
Tyr Thr His Ile Glu Ala Thr Val Ser Gly Gly Phe Tyr Gly Lys Asn
            530                 535                 540
Ala Ile Glu Met Gly Gly Ser Phe Ser Phe Pro Gly Asn Ala Pro Glu
545                 550                 555                 560
Gly Lys Gln Glu Lys Ala Ser Val Val Phe Gly Ala Lys Arg Gln Gln
            565                 570                 575
Leu Val Gln
```

( 2 ) INFORMATION FOR SEQ ID NO:2:

( i ) SEQUENCE CHARACTERISTICS:
    ( A ) LENGTH: 691 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:2:

```
Cys Leu Gly Gly Gly Gly Ser Phe Asp Leu Asp Ser Val Asp Thr Glu
 1               5                  10                  15

Ala Pro Arg Pro Ala Pro Lys Tyr Gln Asp Val Ser Ser Glu Lys Pro
            20                  25                  30

Gln Ala Gln Lys Asp Gln Gly Gly Tyr Gly Phe Ala Met Arg Leu Lys
        35                  40                  45

Arg Arg Asn Trp Tyr Pro Gly Ala Glu Glu Ser Glu Val Lys Leu Asn
    50                  55                  60

Glu Ser Asp Trp Glu Ala Thr Gly Leu Pro Thr Lys Pro Lys Glu Leu
 65                 70                  75                  80

Pro Lys Arg Gln Lys Ser Val Ile Glu Lys Val Glu Thr Asp Gly Asp
                85                  90                  95

Ser Asp Ile Tyr Ser Ser Pro Tyr Leu Thr Pro Ser Asn His Gln Asn
            100                 105                 110

Gly Ser Ala Gly Asn Gly Val Asn Gln Pro Lys Asn Gln Ala Thr Gly
        115                 120                 125

His Glu Asn Phe Gln Tyr Val Tyr Ser Gly Trp Phe Tyr Lys His Ala
    130                 135                 140

Ala Ser Glu Lys Asp Phe Ser Asn Lys Ile Lys Ser Gly Asp Asp
145                 150                 155                 160

Gly Tyr Ile Phe Tyr His Gly Glu Lys Pro Ser Arg Gln Leu Pro Ala
                165                 170                 175

Ser Gly Lys Val Ile Tyr Lys Gly Val Trp His Phe Val Thr Asp Thr
            180                 185                 190

Lys Lys Gly Gln Asp Phe Arg Glu Ile Ile Gln Pro Ser Lys Lys Gln
        195                 200                 205

Gly Asp Arg Tyr Ser Gly Phe Ser Gly Asp Gly Ser Glu Glu Tyr Ser
    210                 215                 220

Asn Lys Asn Glu Ser Thr Leu Lys Asp Asp His Glu Gly Tyr Gly Phe
225                 230                 235                 240

Thr Ser Asn Leu Glu Val Asp Phe Gly Asn Lys Lys Leu Thr Gly Lys
                245                 250                 255

Leu Ile Arg Asn Asn Ala Ser Leu Asn Asn Thr Asn Asn Asp Lys
            260                 265                 270

His Thr Thr Gln Tyr Tyr Ser Leu Asp Ala Gln Ile Thr Gly Asn Arg
        275                 280                 285

Phe Asn Gly Thr Ala Thr Ala Thr Asp Lys Lys Glu Asn Glu Thr Lys
    290                 295                 300

Leu His Pro Phe Val Ser Asp Ser Ser Leu Ser Gly Gly Phe Phe
305                 310                 315                 320

Gly Pro Gln Gly Glu Glu Leu Gly Phe Arg Phe Leu Ser Asp Asp Gln
                325                 330                 335

Lys Val Ala Val Val Gly Ser Ala Lys Thr Lys Asp Lys Leu Glu Asn
            340                 345                 350

Gly Ala Ala Ala Ser Gly Ser Thr Gly Ala Ala Ala Ser Gly Gly Ala
        355                 360                 365

Ala Gly Thr Ser Ser Glu Asn Ser Lys Leu Thr Thr Val Leu Asp Ala
```

-continued

```
                    370                            375                            380
        Val  Glu  Leu  Thr  Leu  Asn  Asp  Lys  Lys  Ile  Lys  Asn  Leu  Asp  Asn  Phe
        385                      390                      395                      400
        Ser  Asn  Ala  Ala  Gln  Leu  Val  Val  Asp  Gly  Ile  Met  Ile  Pro  Leu  Leu
                            405                      410                      415
        Pro  Lys  Asp  Ser  Glu  Ser  Gly  Asn  Thr  Gln  Ala  Asp  Lys  Gly  Lys  Asn
                            420                      425                      430
        Gly  Gly  Thr  Glu  Phe  Thr  Arg  Lys  Phe  Glu  His  Thr  Pro  Glu  Ser  Asp
                       435                      440                      445
             Lys  Lys  Asp  Ala  Gln  Ala  Gly  Thr  Gln  Thr  Asn  Gly  Ala  Gln  Thr  Ala
             450                      455                           460
        Ser  Asn  Thr  Ala  Gly  Asp  Thr  Asn  Gly  Lys  Thr  Lys  Thr  Tyr  Glu  Val
        465                      470                      475                      480
        Glu  Val  Cys  Cys  Ser  Asn  Leu  Asn  Tyr  Leu  Lys  Tyr  Gly  Met  Leu  Thr
                            485                      490                      495
        Arg  Lys  Asn  Ser  Lys  Ser  Ala  Met  Gln  Ala  Gly  Gly  Asn  Ser  Ser  Gln
                       500                      505                           510
        Ala  Asp  Ala  Lys  Thr  Glu  Gln  Val  Glu  Gln  Ser  Met  Phe  Leu  Gln  Gly
                  515                      520                      525
        Glu  Arg  Thr  Asp  Glu  Lys  Glu  Ile  Pro  Thr  Asp  Gln  Asn  Val  Val  Tyr
             530                      535                      540
        Arg  Gly  Ser  Trp  Tyr  Gly  His  Ile  Ala  Asn  Gly  Thr  Ser  Trp  Ser  Gly
        545                      550                      555                      560
        Asn  Ala  Ser  Asp  Lys  Glu  Gly  Asn  Arg  Ala  Glu  Phe  Thr  Val  Asn
                            565                      570                           575
        Phe  Ala  Asp  Lys  Lys  Ile  Thr  Gly  Lys  Leu  Thr  Ala  Glu  Asn  Arg  Gln
                       580                      585                      590
        Ala  Gln  Thr  Phe  Thr  Ile  Glu  Gly  Met  Ile  Gln  Gly  Asn  Gly  Phe  Glu
                  595                      600                      605
        Gly  Thr  Ala  Lys  Thr  Ala  Glu  Ser  Gly  Phe  Asp  Leu  Asp  Gln  Lys  Asn
             610                      615                      620
        Thr  Thr  Arg  Thr  Pro  Lys  Ala  Tyr  Ile  Thr  Asp  Ala  Lys  Val  Lys  Gly
        625                      630                      635                      640
        Gly  Phe  Tyr  Gly  Pro  Lys  Ala  Glu  Glu  Leu  Gly  Gly  Trp  Phe  Ala  Tyr
                            645                      650                           655
        Pro  Gly  Asp  Lys  Gln  Thr  Glu  Lys  Ala  Thr  Ala  Thr  Ser  Ser  Asp  Gly
                       660                      665                           670
        Asn  Ser  Ala  Ser  Ser  Ala  Thr  Val  Val  Phe  Gly  Ala  Lys  Arg  Gln  Gln
                  675                      680                      685
        Pro  Val  Gln
             690
```